United States Patent [19]

O'Neill et al.

[11] Patent Number: 5,395,984
[45] Date of Patent: Mar. 7, 1995

[54] PROCESS FOR PREPARING 2-PHENYL-1,3-PROPANEDIOL

[75] Inventors: Patrick O'Neill, Arklow; Henry Doran, Bray, both of Ireland

[73] Assignee: Schering Corporation, Kenilworth, N.J.

[21] Appl. No.: 230,359

[22] Filed: Apr. 20, 1994

[51] Int. Cl.$^6$ ............................................. C07C 33/26
[52] U.S. Cl. ....................................... 568/811; 568/814
[58] Field of Search ................................. 568/811, 814

[56] References Cited

U.S. PATENT DOCUMENTS 4,868,327  9/1989  Stiefel ................................. 568/811
5,072,056  12/1991  Stiefel ................................. 568/814

OTHER PUBLICATIONS

Kamenka, et al., *Bull. Chem. Soc. France*, (No. 6) 2281–2286 (1972).
Kamenka, et al., *Bull Chem. Soc. France*, (No. 9) 3432–3441 (1972).
R. Davies, *J. Chem. Soc. Perkin Trans. II*, 13, 1399–1411 (1975).

*Primary Examiner*—Werren B. Lone
*Attorney, Agent, or Firm*—Paul A. Thompson

[57] ABSTRACT

Described is a process for preparing 2-phenyl-1,3-propanediol by converting the 2-nitro-2-phenyl-1,3-propanediol to a nitro-dioxane of the formula

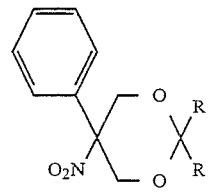

wherein the groups R are both $C_1$–$C_6$ alkyl or together comprise a $C_5$–$C_6$ cycloalkyl group, or wherein one R group is H and the other is phenyl; hydrogenolysis of the nitro-dioxane to give a dioxane of the formula

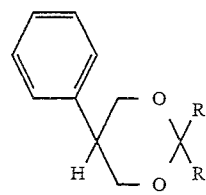

wherein R is as defined above; and hydrolyzing the dioxane to form 2-phenyl-1,3-propanediol.

10 Claims, No Drawings

PROCESS FOR PREPARING 2-PHENYL-1,3-PROPANEDIOL

BACKGROUND OF THE INVENTION

The compound 2-phenyl-1,3-propanediol (PPD) is a key intermediate in the synthesis of the anti-epileptic drug felbamate. The current commercial preparation of PPD utilizes essentially the same procedure as disclosed in U.S. Pat. No. 4,868,327, which comprises hydrogenolysis of 2-phenyl-2-nitro-1,3-propanediol (I). In the current process, the hydrogenolysis is carried out in MeOH using palladium on $CaCO_3$ as a catalyst, with PdO on $CaCO_3$ giving the best results for commercial scale production.

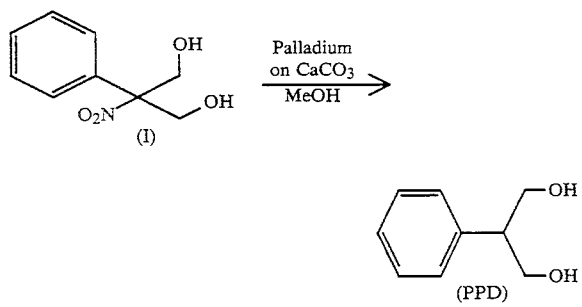

The current process suffers from several problems which are severely exacerbated when the process is utilized for commercial scale production of PPD. These problems include: (a) the necessity of very high solvent volumes for consistent results [$\geq 10$ volumes of MeOH based on the amount of compound (I)]; (b) the need to use PdO on $CaCO_3$, an expensive and difficult to recover catalyst, for optimal performance; (c) a slow rate of reaction with total reaction time being unpredictable and ranging from 20 to 40 hours; (d) a high sensitivity to temperature, with unacceptably slow reaction rates occurring below 25° C. and a build up in the level of impurities at reaction temperatures over 25° C.; and (e) the necessity of frequently venting gaseous by-products of the reaction (typically every 3 h). In addition, the current process is extremely sensitive to other variables, such as the purity of starting material, i.e., compound (I), the quality of the palladium catalyst, the type of reaction vessel used (e.g. the reaction is generally more consistent in glass lined reactors as compared to stainless steel vessels), and the manner in which by-product gases are vented.

The highly unpredictable nature of the current process is predominantly due to the formation of $NH_3$ as a by-product gas during the hydrogenolysis of compound (I). Compound (I) is very sensitive to base, undergoing a base-catalyzed dehydroxymethylation side-reactions to form compounds (II) and (III), which then undergo hydrogenolysis to form a variety of impurities. In particular 2-phenylethanol is generally formed as an impurity during the current process, with levels of this impurity as high as 15%.

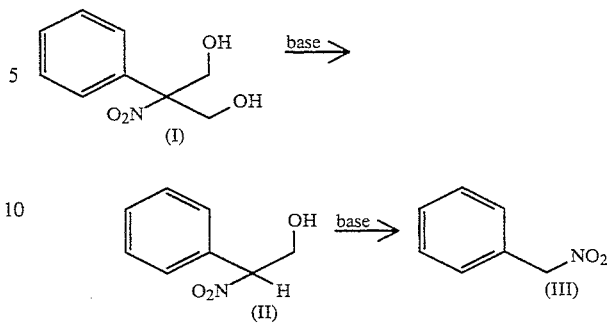

SUMMARY OF THE INVENTION

The present invention avoids the problems of the current process by converting (I) to a cyclic ketal or acetal derivative prior to hydrogenolysis. Hydrogenolysis of such derivatives of compound (I) then proceeds without the base-catalyzed degradation side-reactions that plague the current process. Following hydrogenolysis the cyclic ketal or acetal group is readily removed to give PPD.

The process of the present invention can be carried out using inexpensive and readily available catalysts, at much higher substrate concentrations, with much shorter and more consistent reaction times, and overall yields comparable to the current process. In addition, the instantly claimed process is not equipment sensitive and does not require frequent venting of the reaction mixture. Moreover, the process of the present invention can be carried out without isolation of the acetal or ketal intermediates, and is therefore both cost effective and commercially efficient.

More specifically, the present invention comprises a process for preparing 2-phenyl-1,3-propanediol comprising:

(a) treating 2-nitro-2-phenyl-1,3-propanediol with benzaldehyde, a compound of the formula $(R^1)_2C(OCH_3)_2$ or with a combination of $HC(OCH_3)_3$ and a ketone of the formula $(R^1)_2C=O$, wherein each $R^1$ is $C_1$–$C_6$ alkyl or the two $R^1$ groups together with the carbon to which they are attached comprise a $C_5$–$C_6$ cycloalkyl group, in the presence of an organic acid to form a nitro-dioxane of the formula

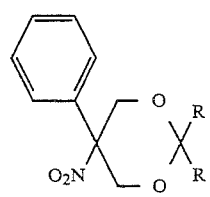

wherein the groups R are both $C_1$–$C_6$ alkyl or together with the carbon to which they are attached comprise a $C_5$–$C_6$ cycloalkyl group, or wherein one R group is H and the other is phenyl;

(b) reacting the nitro-dioxane with $H_2$, gas in the presence of a hydrogenation catalyst and an alcohol solvent to give a dioxane of the formula

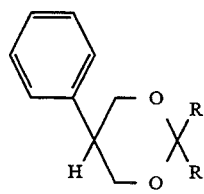

wherein R is as defined above; and (c) hydrolyzing the dioxane of step (b):
  (i) where both R groups are $C_1$–$C_6$ alkyl or together with the carbon to which they are attached comprise a $C_5$–$C_6$ cycloalkyl group, by treating with aqueous acid; or
  (ii) where one R group is H and the other is phenyl, by treating with $H_2$ gas in the presence of a hydrogenation catalyst, an organic acid and an alcohol solvent; to form 2-phenyl-1,3-propanediol.

DETAILED DESCRIPTION

As used herein, the term

"hydrogenation catalyst" means a palladium catalyst such as Pd on carbon;

"organic acid" means an organic compound bearing an acidic functional group, such as a sulfonic acid moiety, which is capable of catalyzing the formation of a cyclic ketal or acetal, with preferred organic acids including p-toluenesulfonic acid;

"alcohol solvent" means a $C_1$–$C_6$ alcohol, such as methanol, ethanol or iso-propanol;

"aqueous base" means a solution of a basic compound, such as NaOH, KOH, Ca(OH)$_2$, NH$_4$OH, Mg(OH)$_2$, CaCO$_3$, Na$_2$CO$_3$, K$_2$CO$_3$, preferably NaOH or KOH, in water; and "aqueous acid" means a solution of an acid in water capable of hydrolyzing a cyclic ketal. Preferred is a solution of HCl in water.

The following solvents and reagents employed in the process of the present invention are identified by the abbreviations indicated: isopropanol (iPrOH); methanol (MeOH); triethylamine (Et$_3$N); p-toluenesulfonic acid (p-TsOH).

The present invention comprises a process as shown in Reaction Scheme I for preparing PPD.

Reaction Scheme I

Step (a)

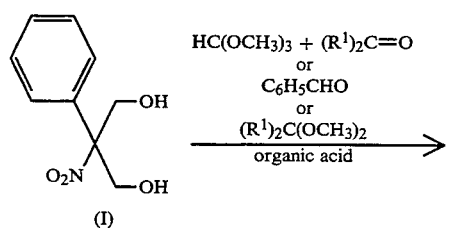

-continued
Reaction Scheme I

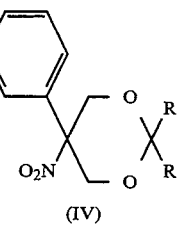

(IV)

[(IVa) where R = $R^1$
(IVb) where one R is H and the other is $C_6H_5$]

Step (b)

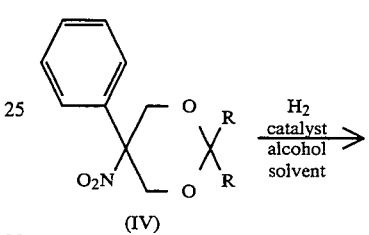

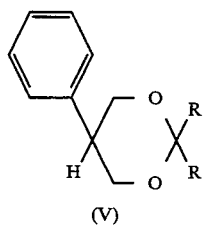

(V)

[(Va) where R = $R^1$
(Vb) where one R is H and the other is $C_6H_5$]

Step (c)(i)

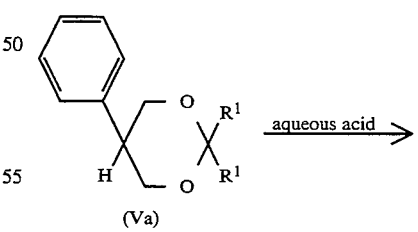

or

Step (c)(ii)

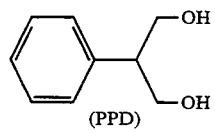

(PPD)

-continued
Reaction Scheme I

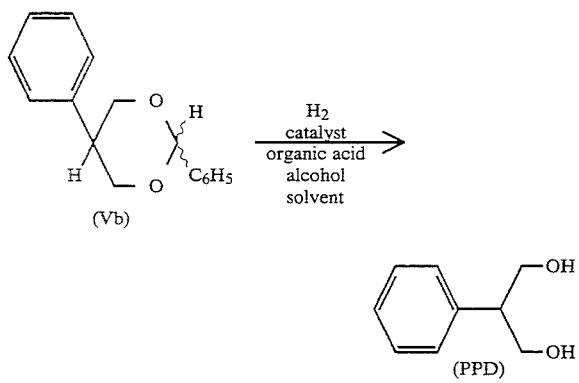

In Step (a), the starting compound (I) is preferably treated with $HC(OCH_3)_3$ and a ketone of the formula $(R^1)_2C=O$, wherein $R^1$ is as defined above, preferably $R^1=CH_3$, in the presence of an organic acid, preferably p-TsOH, at 20°–120° C., preferably at 20°–80° C., more preferably at 20°–60° C., and most preferably at 30°–40° C., to form a compound of the formula (IV). The reaction mixture is then treated with a tri($C_1$–$C_6$ alkyl)amine base, preferably $Et_3N$, prior to hydrogenolysis. Compound (IV) is optionally isolated by crystallization from an alcohol/water mixture, preferably iPrOH/water, using standard methods.

Alternatively, the starting compound (I) is treated with a compound of the formula $(R^1)_2C(OCH_3)_2$, wherein $R^1$ is as defined above, preferably $R^1=CH_3$, in the presence of an organic acid, preferably p-TsOH, at 20°–120° C., preferably at 20°–80° C., more preferably at 20°–60° C., and most preferably at 30°–40° C., to form a compound of the formula (IV). The reaction mixture is then treated with a tri($C_1$–$C_6$ alkyl)amine base, preferably $Et_3N$, prior to hydrogenolysis. Compound (IV) is optionally isolated by crystallization from an alcohol/water mixture, preferably iPrOH/water, using standard methods.

In another alternative, the starting compound (I) is treated with benzaldehyde in the presence of a suitable organic solvent, preferably toluene, at a temperature of 20°–120° C., preferably at 50°–120° C., and most preferably at reflux temperature, followed by treatment with either a tri($C_1$–$C_6$ alkyl)amine base, preferably $Et_3N$, or an aqueous base, such as NaOH (aqueous), to remove the organic acid. The compound (IV) is isolated prior to hydrogenolysis by recrystallization from toluene.

In Step (b), compound (IV) is preferably used without isolation and is reacted with $H_2$ gas at a pressure of 1–100 psi, preferably at 20–60 psi and most preferably at 45–55 psi, in the presence of a hydrogenation catalyst, preferably Pd on carbon, such as 5% Pd on carbon, to give a compound of the formula (V). The reaction of Step (b) is carried out using an alcohol solvent, preferably MeOH or iPrOH, at a temperature of 20°–80° C., preferably at 40°–60° C., and most preferably at 45°–55° C.

In Step (c), the compound (V) is hydrolyzed to form PPD. Where R is $R^1$, i.e., for compounds of the formula (Va), Step (c) comprises Step (c)(i) wherein compound (Va) is treated with an aqueous acid, preferably aqueous HCl, at 0°–100° C., preferably at 20°–80° C., preferably at 40°–60° C., and most preferably at 45°–55° C., for form PPD.

Alternatively, where one R is H and the other is phenyl, i.e., for compounds of the formula (Vb), Step (c) comprises Step (c)(ii) wherein compound (Vb) is treated with $H_2$ gas in the presence of a hydrogenation catalyst, preferably Pd on carbon, such as 5% Pd on carbon, an organic acid, preferably p-TsOH, and an alcohol solvent, preferably MeOH or iPrOH, at a temperature of 0°–100° C., preferably at 20°80° C., more preferably at 40°–60° C., and most preferably at 45°–55° C., and at a pressure of 1–100 psi, preferably at 20–60 psi and most preferably at 45–55 psi, to give PPD.

The starting compound 2-nitro-2-phenyl-1,3-propanediol is known and can be prepared by established methods.

The product of Reaction Scheme I, Step (b), as described above may contain small amounts of basic impurities. These impurities are typically amines of the formula (VI) and hydroxylamines of the formula (VII)

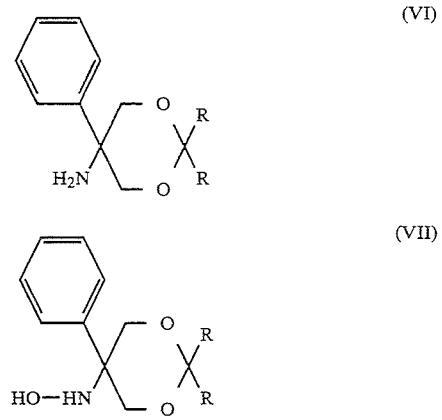

wherein R is as defined above. These impurities, along with any residual p-TsOH can be removed by dissolving the product of Step (b) in a suitable organic solvent, such as toluene, and extracting with an aqueous solution of $H_3PO_4$. The organic solution of the product of Step (b) can be used directly in Step (c). Alternatively, the organic solvent can then be removed via standard methods to give the purified product of Step (b) for use in Step (c).

The following examples are illustrative of the process of the present invention.

EXAMPLE 1

Step (a):

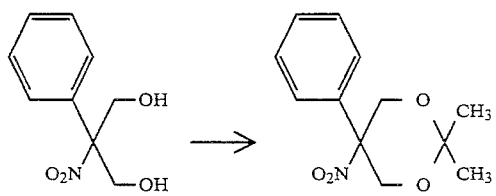

Combine 150 g (0.76 mole) of 2-nitro-2-phenyl-1,3propanediol and 88.3 g (1.52 mole) of acetone and 1.5 g (7.95 mmol) of p-TsOH. Stir the mixture at room temperature, then slowly add 161.4 g (1.52 mole) of $HC(OCH_3)_3$, while keeping the reaction temperature below 40° C. Stir the resulting mixture at 35°–40° C. for about 30 min., then vacuum distill to remove the low boiling components of the mixture. Add 1.0 g (9.9 mmol) of Et₃N, then add 450 mL of either iPrOH or MeOH and analyze the resulting solution by HPLC. The solution contains the desired product (99.0% yield by HPLC) and is used directly in Step (b).

Step (b):

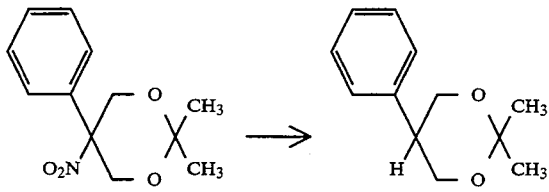

Combine the solution of Step (a) and 9.0 g of 5% Pd on charcoal (50% water-wet), purge with N₂ and heat the mixture to 50° C. Replace the N₂ with H2 and pressurize to 50 psi. The mixture is kept at 50° C. and 50 psi for 4.5 h, then cooled to room temperature while maintaining the pressure at 50 psi. Vent the H₂, purge with N₂, then filter the reaction mixture through celite ®. Concentrate the filtrate in vacuo to give 146 g (100% yield) of the product.

Step (c):

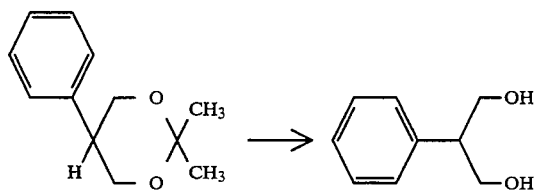

Combine 146 g of the product of Step (b) with 75 mL of toluene and 200 mL of 0.2M H₃PO₄ (aqueous) and stir the mixture for 0.5 h. Separate the layers and combine the organic solution with 150 mL of water and 2 mL of concentrated HCl and stir the mixture at 50° C. for 0.5 h. Concentrate/in vacuo at 50°–60° C., then at 90° C. to give a residue. Dissolve the residue in 450 mL of toluene and reflux over a Dean Stark trap for 0.5 hours to remove residual water. Cool the toluene solution to 40° C. and add a seed crystal of PPD. Allow the mixture to stand at 30°–40° C. for 1 h, then cool to 0°–10° C. for 1 h. Filter, wash the solid with toluene, then air dry the solid to give 106.5 g (92% yield) of the product PPD. mp=52°–54° C.

EXAMPLE 2

Step (a):

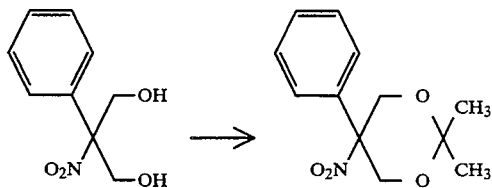

Combine 100 g (0.51 mole) of 2-nitro-2-phenyl-1,3propanediol and 125 mL (1.02 mole) of 2,2-dimethoxypropane. Heat the mixture to 40° C. and add 1.0 g (5.3 mmol) of p-TsOH, then stir at 30°–40° C. for 1 h. Place the mixture under vacuum to distill off 44 mL MeOH (which forms as a byproduct of the reaction.)

Neutralize the p-TsOH by adding 0.55 g of Et₃N, then add 500 mL of iPrOH and heat the mixture to 50°–55° C. until all solids have dissolved to give a solution of the product in iPrOH.

Step (b):

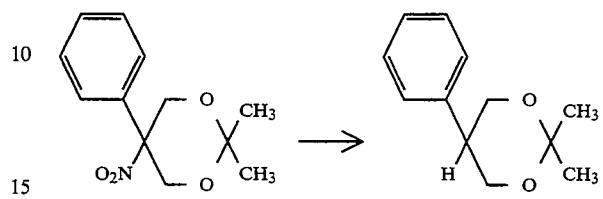

Combine the solution of Step (b) and 6.0 g of 5% Pd on carbon (60% water-wet), heat the mixture to 50° C. and purge with N₂. Pressurize with H₂ to 50 psi and maintain at 50° C. and 50 psi for 4 h. Vent the H₂, purge with N₂, then filter through celite ®. Concentrate the filtrate in vacuo to give 97.3 g (100% yield) of product.

Step (c):

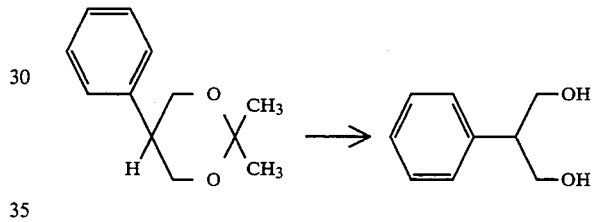

Hydrolyze the product of Step (a) with aqueous HCl as described in Example 2, Step (c) to give 70.3 g (92% yield) of the product PPD. mp=52°–54° C.

EXAMPLE 3

Step (a):

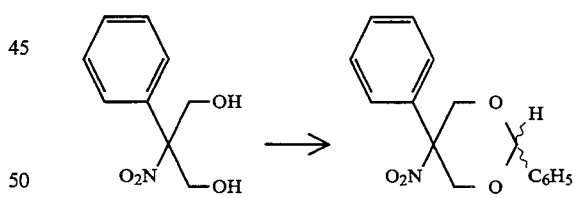

Combine 200 g (1.015 mole) of 2-nitro-2-phenyl-1,3propanediol, 1 L of toluene and 2.0 g (10.5 mmol) of p-TsOH. Add 116 g (1.094 mole) of benzaldehyde and heat the mixture to reflux over a Dean Stark trap for 1 h. A total of 18 mL (1.0 mole) of water is collected during this time. Cool the mixture to 80° C., then add 500 mL of 5% NaOH (aqueous) and continue heating at 80° C. for 30 min. Separate the layers and wash the toluene solution with 800 mL of water at 80° C. Dry the solution by azeotropic distillation, then cool to room temperature to allow crystallization of the product. Cool the mixture to 0°–10° C. for 1 h., then filter and dry the solid by heating overnight at 60° C. under vacuum to give 262.7 g (91% yield) of the product. mp=119°–126° C. (The product is an 84:16 mixture of two stereoisomers as determined by chromatography.)

Step (b):

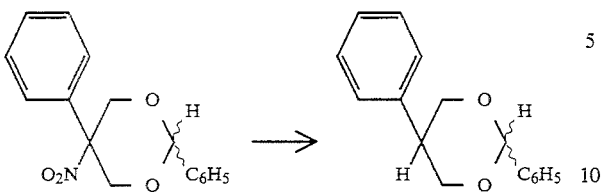

Combine 55.8 g (0.196 mole) of the product of Step (a), 1.9 g of 5% Pd on carbon (61% water-wet) and 200 mL of iPrOH, in an autoclave. Seal the autoclave, purge with N₂ gas, then pressurize with H₂ gas and heat the mixture to 50° C. at a pressure of about 50 psi for 4.25 hours. Additional H₂ gas is added as necessary to maintain a pressure of about 50 psi. Vent the H₂ and purge with N₂, then filter the mixture through celite®. Concentrate the filtrate in vacuo to give the product 45.6 g (97% yield). The product is used in step C or is recrystallized from iPrOH to give purified product. mp=124.6°–125.6° C.

Step (c):

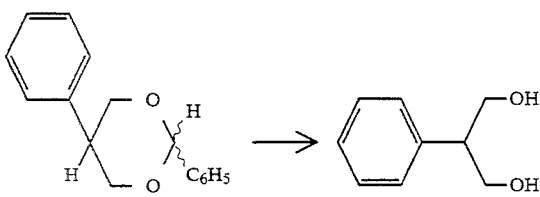

Combine 40.0 g (1.67 mole) of the product of Step (b), 1.0 g (5.26 mmol) of p-TSOH, 2.0 g of 5% Pd on carbon (61% water-wet) and 300 mL of iPrOH. Heat the mixture to 50° C., purge with N₂, then pressurize with H₂ to 50 psi for 1.5 h. Vent the H₂, purge with N₂, then filter and concentrate in vacuo to give a residue. Recrystallize the residue from 100 mL of toluene to give 21.4 g (85% yield) of the product PPD. mp=52°–54° C.

EXAMPLE 4

Step (a):

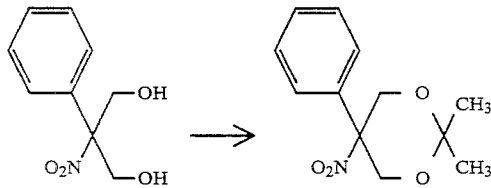

Combine 100 g (0.51 mole) of 2-nitro-2-phenyl-1,3propanediol and 125 mL (1.02 mole) of 2,2-dimethoxypropane. Heat the mixture to 40° C. and add 1.0 g (5.3 mmol) of p-TsOH, then stir at 30°–40° C. for 0.5 h. Place the mixture under vacuum and distill off 44 mL of MeOH (which forms as a by-product of the reaction.) Add 0.55 g (5.5 mmol) of triethylamine, then add 350 mL of iPrOH and heat the mixture to 50°–55° C. until all solids have dissolved. Add 200 mL of hot (50° C.) water, then add a seed crystal of the product and allow the mixture to cool to room temperature over 2 h. Stir the mixture at 0°–10° C. for 1 h, then filter and wash the solid with water. Dry the solid at 67°–70° C. under vacuum for 12 h. to give 113.1 g (94% yield) of the product.

Step (b):

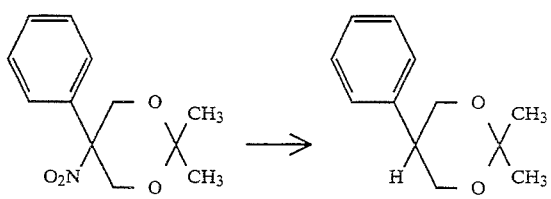

Dissolve 100 g (0.42 mole) of the product of Step (a) in 350 mL of iPrOH by heating to 50°–55° C. Add 5.0 g of 5% Pd on carbon (60% water-wet), heat the mixture to 50° C. and purge with N₂. Pressurize with H₂ to 50 psi and maintain at 50° C. and 50 psi for 4.5 h. Vent the H₂, purge with N₂, then filter through celite®. Concentrate the filtrate in vacuo to give 81.1 g (99% yield) of the product.

Step (c):

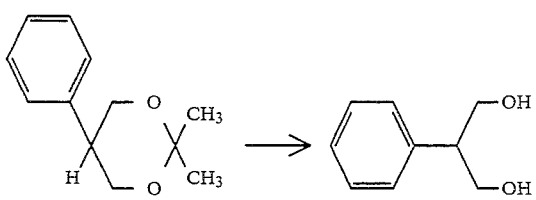

The product of Step (b) is hydrolyzed with aqueous HCl as described in Example 1, Step (c), to give 62.3 g (96% yield) of the product PPD. mp=52°–54° C.

We claim:

1. A process for preparing 2-phenyl-1,3-propanediol comprising the steps:
   (a) treating 2-nitro-2-phenyl-1,3-propanediol with benzaldehyde, a compound of the formula $(R^1)_2C(OCH_3)_2$ or with a combination of $HC(OCH_3)_3$ and a ketone of the formula $(R^1)_2C=O$, wherein each $R^1$ is $C_1$–$C_6$ alkyl or the two $R^1$ groups together with the carbon to which they are attached comprise a $C_5$–$C_6$ cycloalkyl group, in the presence of an organic acid to form a nitro-dioxane of the formula

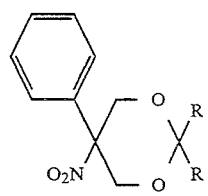

wherein the groups R are both $C_1$–$C_6$ alkyl or together with the carbon to which they are attached comprise a $C_5$–$C_6$ cycloalkyl group, or wherein one R group is H and the other is phenyl;

(b) reacting the nitro-dioxane of step (a) with H₂ gas in the presence of a hydrogenation catalyst and an alcohol solvent to give a dioxane of the formula

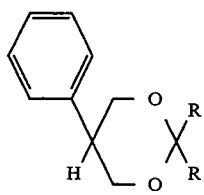

wherein R is as defined above; and (c) hydrolyzing the dioxane of step (b)
  (i) where both R groups are $C_1$–$C_6$ alkyl or together with the carbon to which they are attached comprise a $C_5$–$C_6$ cycloalkyl group, by treating with aqueous acid; or
  (ii) where one R group is H and the other is phenyl, by treating with $H_2$ in the presence of a hydrogenation catalyst, an organic acid and an alcohol solvent; to form 2-phenyl-1,3-propanediol.

2. A process of claim 1 wherein 2-nitro-2-phenyl-1,3propanediol is treated with a compound of the formula $(R^1)_2C(OCH_3)_2$ or with a combination of $CH(OCH_3)_3$ and a ketone of the formula $(R^1)_2C=O$, wherein $R^1$ is $CH_3$, and both R groups are $CH_3$ groups.

3. A process of claim 2 wherein the organic acid of step (a) is toluenesulfonic acid; the hydrogenation catalyst of step (b) is Pd on carbon; the alcohol solvent of step (b) is methanol or isopropanol; and the aqueous acid of step (c)(i) is aqueous HCl.

4. A process of claim 3 wherein step (a) is carried out at 20°–120° C.; step (b) is carried out at 20°–80° C. at a pressure of 1–100 psi; and step (c)(i)is carried out at 0°–100° C.

5. A process of claim 4 wherein: in step (a) 2-nitro-2-phenyl-1,3-propanediol is treated with a combination of $HC(OCH_3)_3$ and a ketone of the formula $(R^1)_2C=O$, wherein $R^1$ is $CH_3$, at 20°–60° C; in step (b) the nitrodioxane of step (a) is treated triethylamine to neutralize the acid of step (a) prior to reacting with $H_2$ gas, and is reacted with $H_2$ gas at 40°–60° C. at pressure of 20–60 psi; in step (c) the dioxane of step (b) is dissolved in toluene and extracted with an aqueous solution of $H_3PO_4$, prior to hydrolysis; and the hydrolysis of step (c) is carried out at 40°–60° C.

6. A process of claim 5 wherein: step (a) is carried out at 30°–40° C.; the reaction with $H_2$ gas in step (b) is carried out at 45°–55° C. at a pressure of 45–55 psi; and the hydrolysis of step (c) is carried out at 45°–55° C.

7. A process of claim 1 wherein 2-nitro-2-phenyl-1,3propanediol is treated with benzaldehyde, and one R group is H and the other is phenyl.

8. A process of claim 7 wherein the organic acid of steps (a) and (c)(ii) is toluenesulfonic acid; the hydrogenation catalyst of steps (b) and (c)(ii) is Pd on carbon; and the alcohol solvent of steps (b) and (c)(ii) is isopropanol.

9. A process of claim 8 wherein step (a) is carried out in the presence of an organic solvent at 20°–120° C.; step (b) is carried out at 20°–80° C. at a pressure of 1–100 psi; and step (c)(i) is carried out at 0°–100° C. at a pressure of 1–100 psi.

10. A process of claim 9 wherein: step (a) is carried out at reflux temperature; step (b) is carried out at 45°–55° C. at a pressure of 45–55 psi; and the hydrolysis of step (c) is carried out at 45°–55° C. at a pressure of 45–55 psi.

* * * * *